US007615030B2

(12) United States Patent
Murphy et al.

(10) Patent No.: US 7,615,030 B2
(45) Date of Patent: Nov. 10, 2009

(54) APPARATUS AND METHOD FOR ADMINISTERING A THERAPEUTIC AGENT INTO TISSUE

(75) Inventors: Kieran Murphy, Baltimore, MD (US); Mario Muto, Napoli (IT)

(73) Assignee: Active O, LLC, Incline Village, NV (US)

(*) Notice: Subject to any disclaimer, the term of this patent is extended or adjusted under 35 U.S.C. 154(b) by 708 days.

(21) Appl. No.: 10/867,215

(22) Filed: Jun. 15, 2004

(65) Prior Publication Data
US 2005/0074501 A1 Apr. 7, 2005

Related U.S. Application Data

(60) Provisional application No. 60/508,300, filed on Oct. 6, 2003.

(51) Int. Cl.
*A61M 37/00* (2006.01)
(52) U.S. Cl. .......................... 604/25; 604/181; 604/187
(58) Field of Classification Search .............. 604/890.1, 604/891.1, 143–147, 181, 184, 187, 23–26; 128/202.25; 424/600; 422/186.07
See application file for complete search history.

(56) References Cited

U.S. PATENT DOCUMENTS

| | | | |
|---|---|---|---|
| 4,632,980 A | 12/1986 | Zee et al. | |
| 4,743,199 A | 5/1988 | Weber et al. | |
| 5,052,382 A * | 10/1991 | Wainwright | 128/202.25 |
| 5,106,589 A | 4/1992 | Conrad | |
| 5,163,904 A | 11/1992 | Lampropoulos et al. | |
| 5,540,898 A | 7/1996 | Davidson | |
| 5,797,872 A | 8/1998 | Ogata et al. | |
| 5,971,722 A | 10/1999 | Maget et al. | |
| 6,073,627 A | 6/2000 | Sunnen | |
| 6,086,552 A | 7/2000 | Bolton | |
| 6,110,431 A * | 8/2000 | Dunder | 422/186.12 |
| 6,134,806 A | 10/2000 | Dhaemers | |

(Continued)

FOREIGN PATENT DOCUMENTS

DE 447936 7/1927

(Continued)

OTHER PUBLICATIONS

Andreula, Cosma et al., "Interventional Spinal Procedures", *European Journal of Radiology 50*, (2004), 112-119.

(Continued)

*Primary Examiner*—Nicholas D Lucchesi
*Assistant Examiner*—Theodore J Stigell
(74) *Attorney, Agent, or Firm*—David Fonda

(57) ABSTRACT

An apparatus for administering a therapeutic agent is provided. The apparatus, in an embodiment, includes an ozone generator connected to a scavenger and an ozone administrator via network of tubing and valves. When activated and the valves placed in the proper position, the ozone generator will fill the ozone administrator with ozone. The ozone generator can then be turned off and the valves moved so that the administrator can be disconnected from the remainder of the apparatus. The administrator is typically in the form of a syringe and needle. Once the syringe and needle is filled with ozone, the needle can be inserted into a tissue and the ozone expressed therefrom into the tissue. Various other apparatuses and methods are also contemplated.

15 Claims, 8 Drawing Sheets

U.S. PATENT DOCUMENTS

| | | | |
|---|---|---|---|
| 6,136,308 | A | 10/2000 | Tremblay et al. |
| 6,204,058 | B1 | 3/2001 | Bolton |
| 6,251,090 | B1 | 6/2001 | Avery et al. |
| 6,391,183 | B1 | 5/2002 | Tanioka et al. |
| 6,620,379 | B1 | 9/2003 | Piuk et al. |
| 6,810,288 | B2 | 10/2004 | Joshi |
| 6,875,018 | B2 | 4/2005 | Lynch et al. |
| 2004/0245087 | A1 | 12/2004 | Lee |
| 2004/0254525 | A1 | 12/2004 | Uber et al. |
| 2005/0010069 | A1 | 1/2005 | Fitchett et al. |
| 2005/0074501 | A1 | 4/2005 | Murphy et al. |
| 2005/0277912 | A1 | 12/2005 | John |
| 2006/0166088 | A1 | 7/2006 | Hokanson et al. |
| 2006/0251551 | A1 | 11/2006 | Johnson |
| 2007/0025890 | A1 | 2/2007 | Joshi et al. |
| 2007/0154363 | A1 | 7/2007 | Joshi et al. |
| 2008/0167650 | A1 | 7/2008 | Joshi et al. |

FOREIGN PATENT DOCUMENTS

| | | |
|---|---|---|
| DE | 25 43 284 A1 | 3/1977 |
| WO | WO-98/10774 | 3/1998 |
| WO | WO-2005032387 | 4/2005 |

OTHER PUBLICATIONS

Andreula, Cosma F., et al., "Minimally Invasive Oxygen-Ozone Therapy for Lumbar Disk Herniation", *American Journal of Neuroradiology 24*, (2003), 996-1000.

Bocci, V. "Biological and Clinical Effects of Ozone. Has Ozone Therapy a Future in Medicine?", *British Journal of Biomedical Science 56*, (1999), 270-279.

Bocci, V. et al., "Ozone in Medicine", *Ozone Science & Engineering 23*, (2001), 207-217.

Bocci, Velio "Oxygen-Ozone Therapy: A Critical Evaluation", *Kluwer Academic Publishers: The Netherlands*, (2002), 43-46.

Bocci, Velio "Ozone: A New Medical Drug", *Springer: The Netherlands*, (2005), 9-11.

Sunnen, Gerard "Ozone in Medicine Bibliography", http://www.medizoneint.com/biblio.html, (Sep. 1999), 1, 3, 5, 7.

List of Medizone Patents and Trademarks, http://www.medizoneint.com/patents.html, 1-2.

Schultz, O Abstract and International Search Report for WO2005032387, (Mar. 2, 2005), 1-6.

European Patent Office Automated Translation of DE2543284, (Oct. 5, 2007), 1-4.

Schultz, O. PCT International Search Report for PCT/IB2004/003706, (Jun. 3, 2005), 1-6.

Schultz, O. PCT Written Opinion of the International Searching Authority for PCT/IB2004/003706, (Jun. 3, 2005), 1-10.

Young, Lee W., PCT International Search Report for PCT/US06/28425, (Jul. 31, 2007), 1-2.

Young, Lee W., PCT Written Opinion of the International Searching Authority for PCT/US06/28525, (Jul. 31, 2007), 1-4.

Ed McCabe, "Scientific And Medical References Proving Ozones's Validity As A Medical Treatment" [online], 1994, [retrieved on Oct. 7, 2004] <url address http://www.ozoneherapy.co.uk/articles/ed_mccabe_ozone_history_and_references.htm>.

Gaetano Morello, "Ozone Therapy: New breakthrough for Back Treatment" [online], [retrieved Nov. 4, 2004] <url address http://www.cleanairassociation.com/6/ca_3.htm>.

M. Muto and F. Avella, "Percutaneous Treatment of Herniated Lumbar Disc By Intradiscal Oxygen-Ozone Injection", Interventional Neuroradiology 4:279-286, 1998.

Young, International Search Report for PCT/US07/25989 sent Mar. 27, 2008, 1-2.

Young, Written Opinion for PCT/US07/25989 sent Mar. 27, 2008, 1-6.

Schell, Office Action for U.S. Appl. No. 11/193,339 sent Dec. 3, 2008, 1-10.

Schultz, Ottmar "European Search Report for App. No. EP08004372", (May 8, 2008),1-8.

Schell, Laura "Office Action for U.S. Appl. No. 11/193,339 mailed on Jul. 6, 2009", (Jul. 6, 2009),1-9.

\* cited by examiner

APPARATUS AND METHOD FOR ADMINISTERING A THERAPEUTIC AGENT INTO TISSUE

PRIORITY CLAIM

The present application claims priority from U.S. Provisional Patent Application No. 60/508,300, filed Oct. 6, 2003, the contents of which are incorporated herein by reference.

FIELD OF THE INVENTION

The present invention relates generally to a method, apparatus and kit for administering a therapeutic agent into tissue and in particular, for the administration of a therapeutic agent such as medical ozone.

BACKGROUND OF THE INVENTION

Back joint disc or tendon pain is a common and potentially debilitating ailment that affects an estimated 80% of the worldwide population at least once in a lifetime. In many instances, the cause of the pain can be attributed to a degenerated intervertebral disc that has further deteriorated into a condition known as disc herniation This occurs when the disc nucleus pulposus extrudes through a tear or fissure in the outer lining of the disk, thereby exerting pressure on spinal nerves. The compression caused by the herniated nucleus leads to inflammation and is directly responsible for the pain felt down the leg (also referred to as sciatica). Available treatments for this type of back pain vary according to the severity of the hernia. If mild, the patient's condition can be appeased with rest and inactivity for an extended period of time. However, for patients suffering from a severe herniation or who do not respond to non-invasive treatment (pharmacological and/or physical therapy), surgical intervention is often recommended. With this invasive treatment come several disadvantages such as:
  i) irreversibility of the procedure
  ii) formation of scar tissue
  iii) slower recovery time
  iv) longer hospital stays Since the late 1950s, many attempts have been made to treat sciatica and lower back pain with percutaneous procedures to avoid surgery. Well known treatments for example are percutaneous discetomy and chemonucleolysis but the cost of these procedures has kept researchers looking for another alternative. It was in 1984 that an Italian orthopedic surgeon by the name of Dr. Cesare Verga first proposed the use of ozone/oxygen mixtures to treat the pathology of a herniated disk. (See for example, http://www.cleanairassociationlcom/6/ca__3.htm, Ozone Therapy: New breakthrough for Back Treatment, by Gaetano Morello, M. D., the contents of which are incorporated herein by reference.)

Other prior art references include: Percutaneous Treatment of Herniated Lumbar Disc by Intradiscal Oxygen-Ozone Injection, M. Muto and F. Avella, Interventional Neuroradiology 4:279-286, 1998.

In other situations such as rheumatoid arthritis, osteoarthritis or a repetitive injury through sports or occupation, such as tennis elbow, frozen shoulder, or house maids knee, inflammation can develop between two surfaces the are involved in allowing joint function, such as a tendon and the sheath or lubricated tube in which that tendon moves. Inflammation such as bursitis in the knee shoulder hip, or other anatomic bursa may benefit from ozone therapy, this includes epicondylitis, and other tendonitis and bursitis, including the wrist, hand and the tendon sheaths of the hand and wrist. Inflammation can occur at a site where a tendon or a ligament insert to bone or pass through a sheath from trauma, tension, over use or disease.

Inflammation can develop through pathologies of any joint, and these may again include the inflammatory arthropatic conditions of rheumatoid arthritis, psoriatic arthritis and the like, or osteoarthritis. Joints that may be involved in these processes that are amenable to ozone injection include the synovial joints such as the, temperomandibular joint, the hip joint, knee joint, ankle joint, elbow joint or sacro-iliac joint. Vertebral facet and sacro-iliac joints may also benefit, inflammatory involvement of joints in the hand, wrist and feet with rheumatoid arthritis, osteoarthritis or a repetitive injury through sports or occupational such as carpal tunnel syndrome.

The inflammatory and arthritic or degenerative discussions described above are usually treated with a combination of anti-inflammatory agents such as ibuprofen, or more powerful drugs such as steroids or chemotherapy such as methotrexate. It is a common medical practice to inject steroid medications or lidocaine directly into the inflamed tissue or joint. This is often done repeatedly. These drugs can be associated with side effects of infection and even death from gastric ulcer bleeding or immunosurpression and infection. We believe that ozone therapy whether as a liquid or a gas would have advantages over the current practice.

Lavage of a surgical space prior to placement of a permanent surgical implant such as a hip or knee prosthesis, or pacemaker or treatment of an infected joint can be facilitated by the use of medical ozone as a sterilizing substance. Similarly a colostomy stoma can be created such that the adhesive disk is infused with a ozone as a liquid or gas to aid in healing and inhibit infection. The post surgical recovery from stemotomy after cardiac surgery is often complicated wound infection. Placement of a resorbable catheter in the wound that could be irrigated with ozone liquid or gas would aid healing. Indeed any wound could have a resorbable multisided hole catheter placed in it to allow ozone be injected through it. This would have anti-infective, analgesic and promote wound healing properties. This would shorten recovery time and decrease complication rates after surgery.

Enhance liquid ozone could be applied to the wound/surgical site healing at a site of high probability of infection such an abdominal incision/wound after appendectomy, or urgent colectomy with colostomy or after percutaneous endoscopic cholecystectomy.

Endoscopic procedural infusion of ozone and trans catheter infusion of ozone can be used to inhibit the complications endoscopic medical intervention or image guided or non-image guided catheter based intervention for example in endoscopic evaluation of the pancreatic duct.

Dental injection of liquid or gas ozone may augment the preparation and repair of dental cavities, and aid in reduction of root canal inflammation or periodontal disease.

There are veterinary applications of minimally invasive ozone administration in animals diseased with disc and degenerative syndromes. Few other options are available in that arena. Some animals are destroyed due to debilitating pain secondary to pain from disc disease, and arthritis.

While the full therapeutic potential of ozone continues to unfold with ongoing research, it is already clear that this form of therapy for the treatment of disc herniation has significant advantages over other surgical and percutaneous procedures. Some of these advantages include:
  fewer clinical and neuroradiological contraindications success rates greater than about 70% in the intervertebral disc little or no recovery time little or no side effects little or no scar tissue formed minimally invasive procedure in effective alternative treatment for which response to conservative management, such as rest and reduced daily activity, has failed to treat As the success of ozone gas therapy continues to gain recognition in the medical arena as a non-invasive alternative for the treatment of disc herniation, current methods of administering an effective dose of the ozone are solely as a gas and are far from optimum. There also lacks a sterile methodology through which the ozone can be delivered selectively to the pain-affected area, i.e. the herniated disk. The gas is unstable with a half life measured in seconds. There are no dedicated medical ozone generators that are disposable single use units. In accordance with this, there is a need for equipment especially designed for the treatment of disc herniation and other medical conditions affecting the body with medical ozone so that it can be done in an efficient and sterile manner. There is a need to develop kits for intervention in inflammatory and degenerative disease, that are disposable, or reusable, but aid in creating sterile, stable, ozone rapidly on demand. The generation of ozone liquid from sterile water would allow storage of injector/generators in all medical dental and veterinary facilities.

SUMMARY OF THE INVENTION

It is therefore an object of the present invention to provide a novel apparatus and method for administering a gas into a tissue that obviates or mitigates at least one of the disadvantages of the prior art.

In a first aspect of the invention there is provided a kit for administering therapeutic gas mixture into soft tissue, wherein said gas mixture includes ozone. The kit can comprise of the following items:

Disinfectant

Drape

Skin preparation material

Local anaesthetics contained in vials

Syringes

Short and long needles, some with side holes

Gantry drape

Radiolucent needle holder

Nonionic x-ray dye-for discogram

Infusion wire

Charcoal ozone scavenger

Steroids contained in vials

A source of ozone either generated as a gas or a liquid in a disposable single use unit that is sterilizable. The ozone can be generated in the delivery system as a battery powered electronic hand held disposable device The ozone generator based in the injector will be available in a variety of sizes, capable of delivering a range of ozone volumes, from 1 cc to 5 cc, but could be made to generate volumes of ozone liquid or gas form 0.1 cc to 1 liter.

It is probable that the commonly used volumes would be between 1 cc and 10 cc allowing for dead space in the connecting tubing/needle etc.

Disposable filtered attachment

Stop cocks

Non-compliant tubing

Post-operative dressing for skin closure

Adhesive bandages with gauze pad in the centre

An example of a local anaesthetic is, but not limited to, Lidocaine HCl

An example of a nonionic x-ray dye is, but not limited to, Omnipaque 300 M.

An example of a post-operative dressing is, but not limited to, Povidone gel.

Any suitable source of ozone can be used such as an ozone generator, the AOS-1M Medical Ozonator or AOS-1MS Stainless Medical Ozonator for example, or a disposable injector filled with ozone.

In another aspect of the invention, there is a method for the treatment of pain caused by a herniated disc and comprising of first identifying the herniated disk using an imaging technique and subsequently injecting a known volume of medical ozone into the disc and paraspinous soft tissues in a sterile manner and environment.

In another aspect of the invention, there is provided an apparatus for administering a therapeutic agent comprising a therapeutic agent generator and a scavenger connected to the generator via a first valve for capturing the therapeutic agent. The therapeutic agent administrator is connectable to the generator via at least one additional valve such that when the valves are in a first position the generator communicates with the administrator for filling the administrator with the agent. When the valves are in a second position the administrator retains the agent therein upon disconnection from the generator, and the scavenger captures any excess agent intermediate the administrator and the generator.

The agent can be gaseous or liquid ozone. The generator can be a medical ozone generator. The medical ozone can be a ratio of oxygen (O2) and ozone (O3).

The ratio of ozone in micro grams to oxygen in milliliters can be about 1 µg/ml, or about 10 µg/ml, or about 20 µg/ml, or about 30 µg/ml, or about 40 µg/ml, or about 50 µg/ml.

The ratio of ozone in micro grams to oxygen in milliliters can be between about 1 µg/ml and about 90 µg/ml. The ratio of ozone to oxygen can be between about 10 µg/ml and about 80 µg/ml. The ratio of ozone to oxygen can be between about 20 µg/ml and about 70 µg/ml. The ratio of ozone to oxygen can be between about 10 µg/ml and about 34 µg/ml. More preferably, the ratio of ozone to oxygen can be between about 27 µg/ml to about 28 µg/ml.

The administrator can be a syringe.

Another aspect of the invention provides a method of treating the pain caused by a herniated disc comprising identifying the herniated disk and injecting medical ozone into the disc and paraspinous soft tissues.

Another aspect of the invention provides a syringe for self-contained generation and administration of a therapeutic agent comprising a barrel for holding the agent, and a plunger for insertion into a first end of the barrel and expressing the agent from a second end of the barrel. The syringe also includes a power supply integrally mounted coaxially with the plunger. The syringe also includes a therapeutic agent generator integrally mounted coaxially with the plunger and in communication with the barrel through a channel in the plunger. The generator is connected to the power supply and mounted coaxially with the plunger. The syringe also includes a switch connected to the power supply such that when the switch is activated the therapeutic agent generator generates the therapeutic agent and fills the barrel therewith.

In another aspect of the invention the ozone can be generated either as a liquid or a gas, in a syringe type structure where the electronics are housed in the area normally occupied by the plunger of the syringe and the anode is in the syringe. The syringes can be any desired volumes, such as those ranging from 1 cc to 60 cc, more preferably 1 cc to 10 ccs. The syringes are typically made of polyethylene to resist the corrosive effect of ozone even in the short time it in contact with the plastic.

Another aspect of the invention provides an implantable apparatus for self-contained generation and administration of a therapeutic agent comprising: a chamber for holding the agent and a catheter for connecting the chamber to an area for administration of the agent. The apparatus also includes a power supply and a therapeutic agent generator in communication with the chamber, the generator connected to the power supply. The apparatus also includes a switch activateable externally by a patient implanted with the apparatus. The switch is connected to the power supply such that when the switch is activated the therapeutic agent generator generates the therapeutic agent and fills chamber therewith.

Another aspect of the invention provides a method of treating pain caused by a herniated disc comprising of the following steps:
 identifying the herniated disk with an imaging device;
 preparation of the skin above the affected area;
 applying local anaesthetics to the operation site;
 inserting a needle down to the disc level at the herniated disc;
 injecting nonionic x-ray dye down the needle;
 performing a discogram of the disc;
 activating an ozone generator external to the patient;
 selecting a specific concentration of O3/O2 gas mixture on the ozone generator;
 attaching a scavenger and a syringe to the ozone generator;
 aspirating the O3/O2 gas mixture into the syringe;
 injecting a predetermined volume of a fixed concentration of ozone/oxygen gas mixture into the disc and paraspinous soft tissues of the disc;
 capturing unused ozone in the charcoal scavenger; and,
 removing all needles;
 dressing the operative site.

BRIEF DESCRIPTION OF THE DRAWINGS

Preferred embodiments of the invention will now be discussed, by way of example only, with reference to the attached Figures, in which.

DETAILED DESCRIPTION OF THE INVENTION

Figure 1:
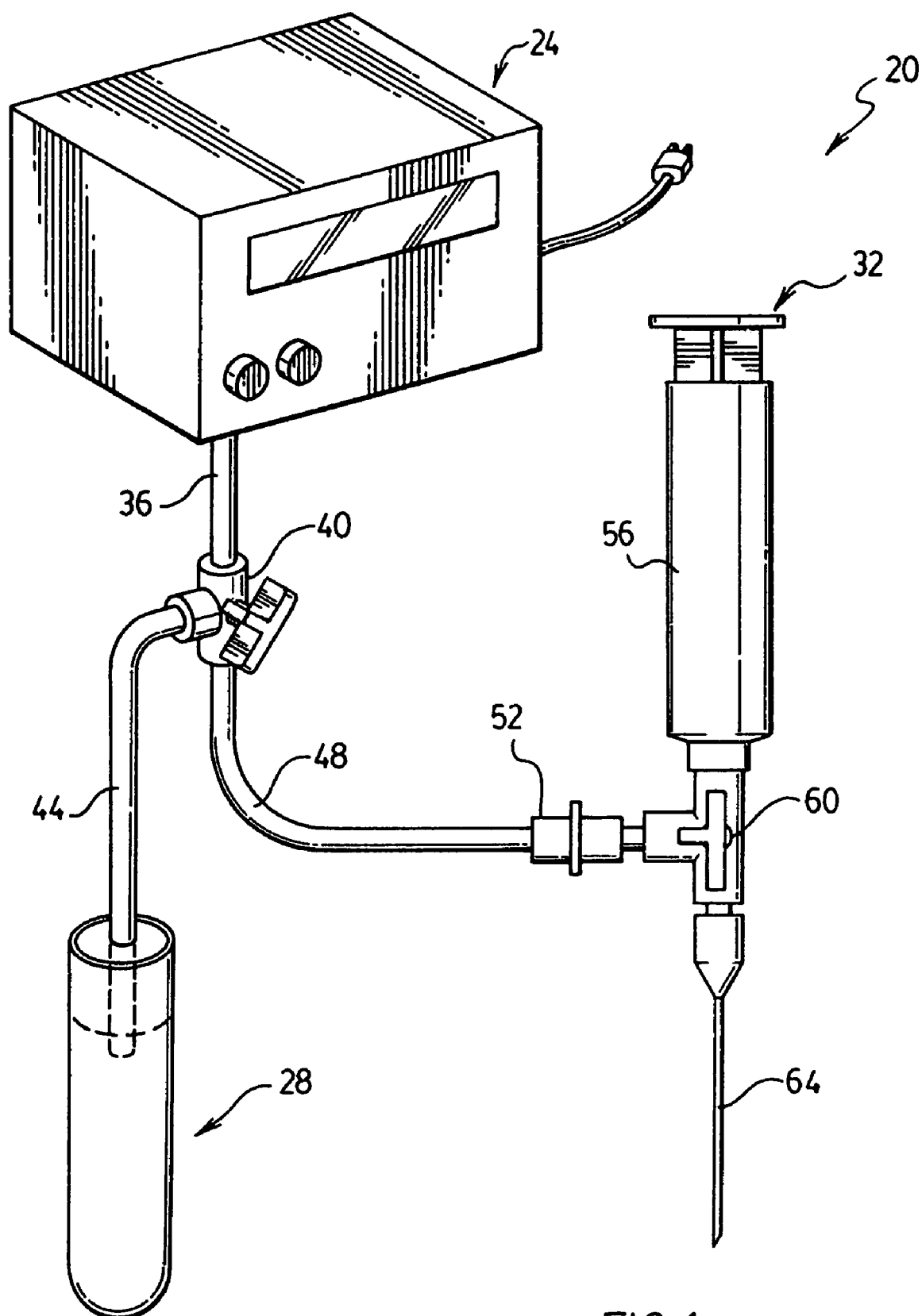
FIG. 1 shows an apparatus for administering a gas into a tissue in accordance with an embodiment of the invention.

Referring now to FIG. 1, an apparatus for administering a therapeutic agent, such as an ozone gas, into a tissue in accordance with an embodiment of the invention is indicated generally at 20. In a present embodiment, apparatus 20 comprises an ozone generator 24 that connects to a charcoal scavenger 28 and an ozone administrator 32. Generator 24 can be based on any known medical ozone generator. Generator 24 connects to scavenger 28 and administrator 32 via a network of flexible tubing and valves for selectively directing the flow of gas therebetween. More specifically, a first segment of tubing 36 connects generator 24 to a three-way valve 40. A second segment of tubing 44 connects valve 40 to scavenger 28. A third segment of tubing 48 connects valve 40 to another valve 52, which in turn connects to administrator 32. The tubing is made of any suitable material, such as silicon of the known medical type, and has a diameter and wall thickness to withstand the pressure of ozone gas being carried therethrough. The valves, also known as stopcocks, are also of the known medical type and have fittings complementary to the various portions of tubing.

Administrator 32 is comprised of a syringe 56, a three-way valve 60, and a needle 64. Syringe 56 is typically made of polyethylene to resist the corrosive effect of ozone, but other materials will occur to those of skill in the art. Three-way valve 60 is releasably connectable directly to valve 52, providing a selective pathway between syringe 56 and generator 24 and/or scavenger 28.

Valve 40 has a first position wherein generator 24 communicates only with tubing 48. Valve 52 has a first position wherein tubing 48 communicates with administrator 32. Valve 60 has a first position wherein syringe 56 communicates only with tubing 48. Thus, when valves 40, 52 and 60 are all in the first position, generator 24 is in communication with syringe 56, and thus when generator 24 is "on", syringe 56 will be filled with ozone. (It is to be noted that in of the Figures attached hereto, for this embodiment subsequent embodiments, the various valves depicted therein are not intended to be shown in any specific position, and are merely illustrated to show their physical orientation in relation to the rest of the components in the apparatus.)

Valve 40 has a second position wherein tubing 44 communicates with both tubing 36 and 48. Valve 52 has a second position wherein tubing 48 is effectively capped, preventing communication between administrator 32 and tubing 48. When valves 40 and 52 are in the second position, any ozone generated by generator 24 is captured by scavenger 28. In a present embodiment, scavenger 28 is of the charcoal type, but any type of scavenger for capturing excess ozone can be used.

Once generator 24 is turned "off" after filling syringe 56 as described above, then when valves 40 and 52 are each moved from their respective first position to their respective second position then any excess ozone still present in tubing 48 and 36 will be captured by scavenger 28 and thereby reduce and/or substantially eliminate the unwanted escape of ozone into the atmosphere where it may harm the operator or other individuals proximal to apparatus 20.

Valve 60 also has a second position wherein syringe 56 is prevented from communicating with either valve 52 (or the open fitting on valve 60 that connects to valve 52), or with needle 64. Thus, once syringe 56 has been filled with ozone, leaving administrator 32 'charged' with ozone, valve 60 will also be placed in its second position to retain the ozone within syringe 56 once administrator 32 is disconnected from valve 52.

Figure 2:
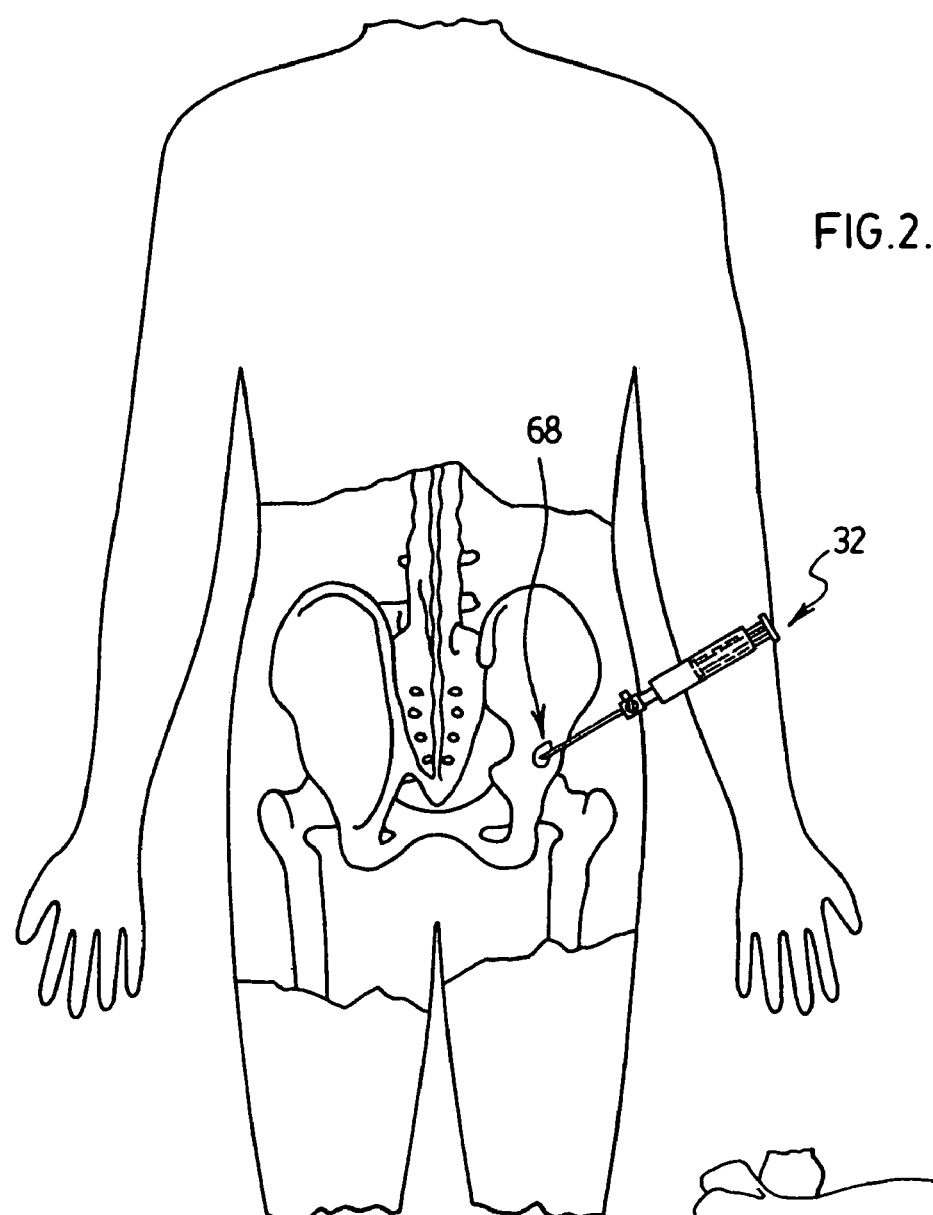
FIG. 2 shows the hip area of a patient where a therapeutic agent can be administered.

Once administrator 32 is charged with ozone, it can be disconnected from the remainder of apparatus 20 so that it can be used to administer ozone to a target area. Thus, valve 60 also has a third position that places syringe 56 in communication with needle 64. Referring now to FIG. 2, when charged, valve 60 can be placed in the second position to prevent ozone from escaping from syringe 56. Administrator 32 can then be disconnected from the remainder of apparatus 20 and then needle 64 can be inserted into tissue (or other target area) where the ozone is to be administered. In FIG. 2, needle 64 is shown inserted into a hip 68. Having inserted needle 64 into hip 68, valve 60 is placed in the third position, allowing syringe 56 to communicate with needle 64. At this point syringe 56 is depressed, and the ozone gas therein is expressed out of needle 64 into hip tissue, thereby providing localized pain relief around hip 68. Such administration of ozone can be helpful to relieve pain after some types of hip surgeries, such as hip replacement, or after bone is harvested from the pelvis to use as a bone graft material.

Figure 3:
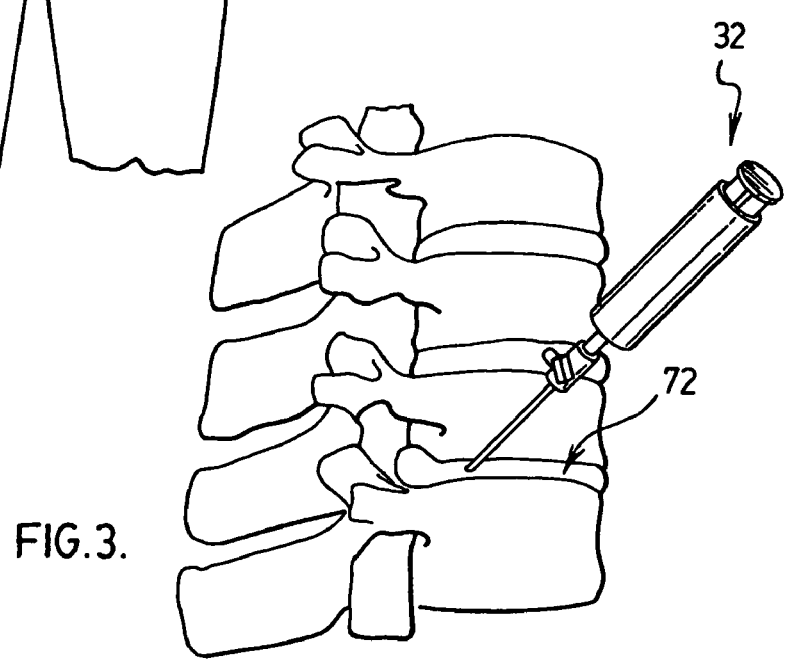
FIG. 3 shows the spinal disc area of a patient where a therapeutic agent can be administered.
Figure 4:
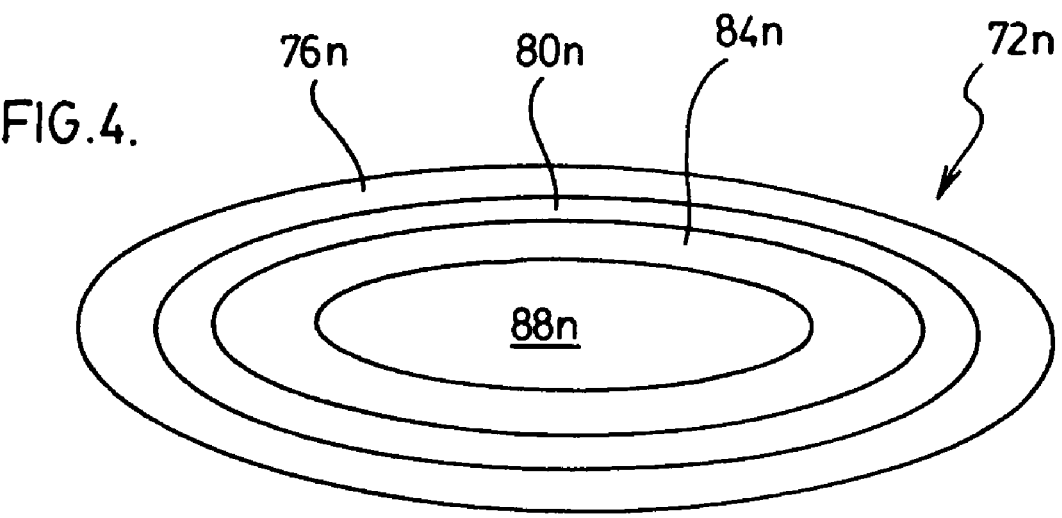
FIG. 4 shows a normal spinal disc.
Figure 5:
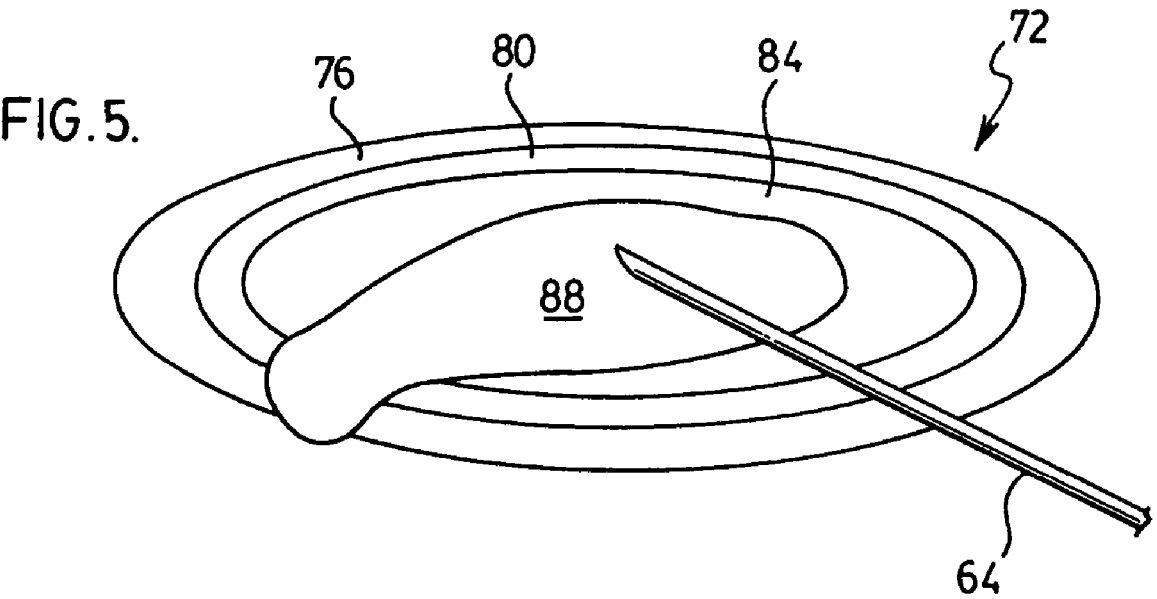
FIG. 5 shows a herniated spinal disc where a therapeutic agent can be administered.

Other types of localized pain relief can also be provided. While FIG. 2 depicts pain relief being provided to hip 68, FIG. 3 depicts the provision of pain relief to a spinal disc 72. By way of background, as seen in FIG. 4 a normal disc is shown in cross section at 72n. Disc 72n has an outer annulus fibrosus 76n, an inner annulus fibrosus 80n, a transition zone 84n, and a nucleus pulposus 88n. However, in FIG. 5, disk 72 is also shown in cross section, wherein nucleus pulposus 88 is protruding, and thereby a cause of pain. However, the administration of ozone into the protruding nucleus pulposus 88 using administrator 32 via needle 64 pain can be relieved and/or substantially eliminated at least temporarily.

It should now be apparent that having administered ozone from administrator 32, administrator 32 can then be reconnected to the remainder of apparatus 20, and the appropriate valves 40, 50 and 62 adjusted to either allow any remaining ozone to be expressed from administrator 32 for capture by scavenger 28, or to refill syringe 56.

Figure 6:
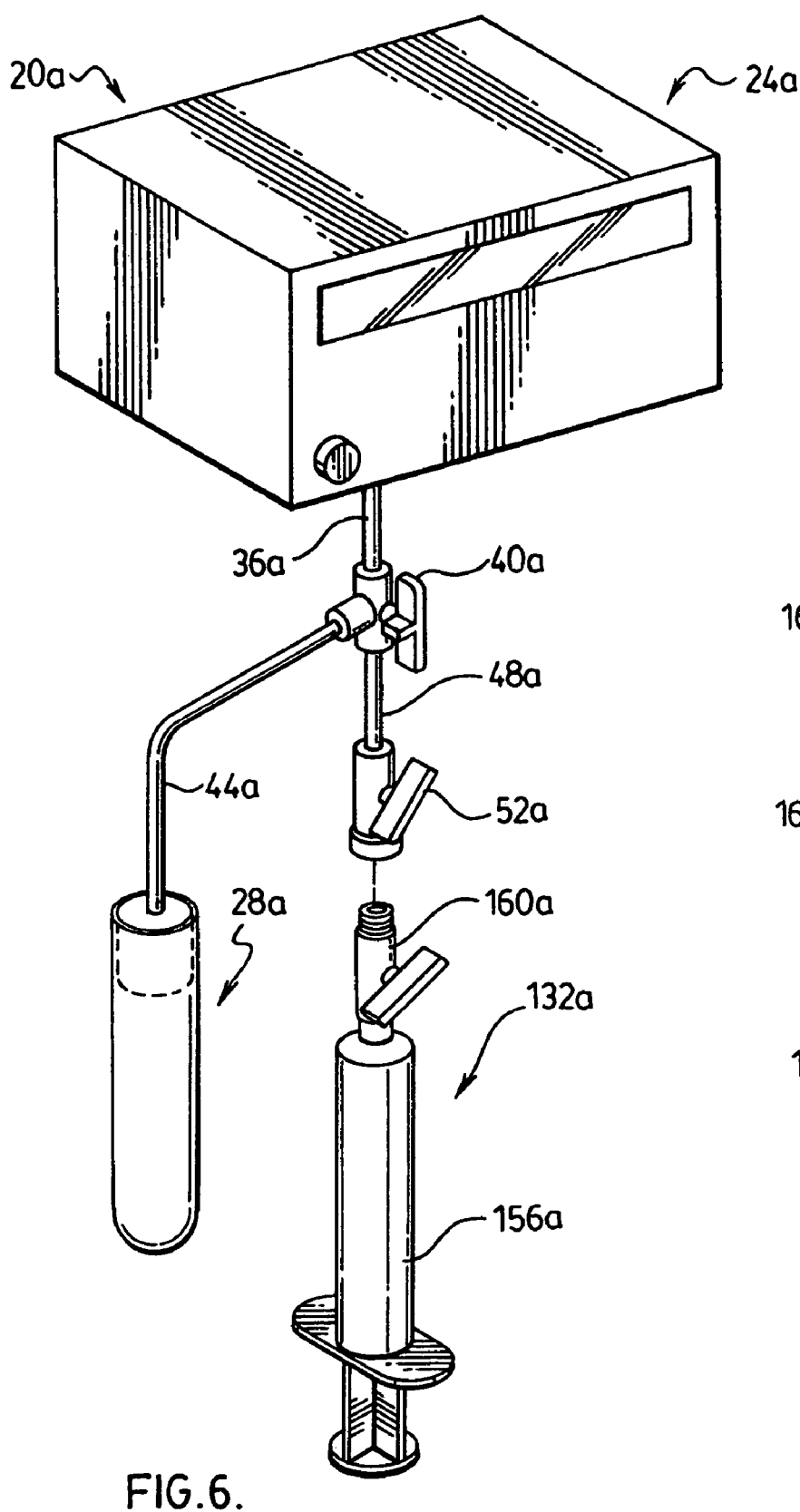
FIG. 6 shows an apparatus for administering a gas into a tissue in accordance with another embodiment of the invention.
Figure 7:
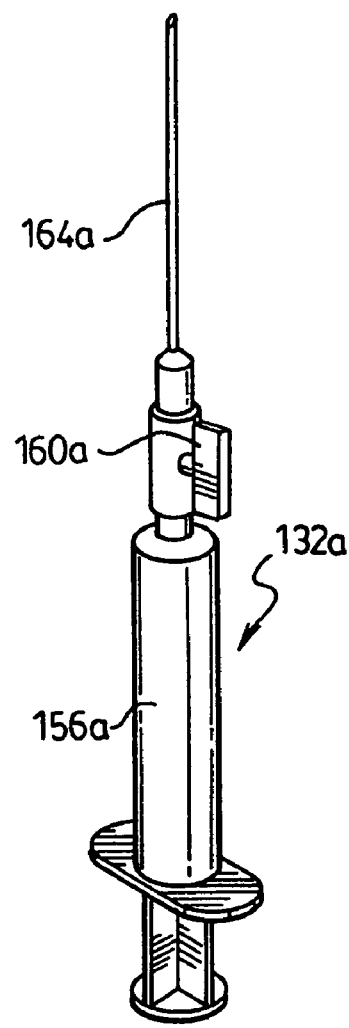
FIG. 7 shows the administrator of FIG. 6 with the needle placed thereon.

Referring now to FIG. 6, an apparatus for administering a gas into a tissue in accordance with another embodiment of the invention is indicated generally at 20a. Apparatus 20a includes many similar components to apparatus 20, and like components are indicated with like references but followed by the suffix "a". In contrast to apparatus 20, however, administrator 132a includes certain differences from administrator 32. Specifically, administrator 132a has a two way valve 160a, one end of which connects to syringe 132a, the other end of which has a fitting to allow administrator 132a to be connected to either valve 52a, as shown in FIG. 6, or to needle 164a as shown in FIG. 7. When administrator 132a is connected to valve 52a as shown in FIG. 6, valves 52a and 160a can be placed in an open position so that syringe 132a communicates with generator 24a. When generator 24a is "on", syringe 132a will be filled with ozone. Once syringe 132a is filled with ozone, valves 52a and 160a can be placed in the closed position, and valve 40a can be turned so that once apparatus 160a is disconnected from valve 52a, any ozone remaining in tubes 48a, 36a or elsewhere in that remaining portion of apparatus 24a can be captured by scavenger 28a.

Having filled syringe 132a with ozone, and closed valve 160a, needle 164a can then be affixed thereto as shown in FIG. 7. Valve 160a can then be selectively opened or closed to allow the administration of ozone to tissue, in much the same manner as previously described in relation to FIGS. 2 and 3.

Figure 8:
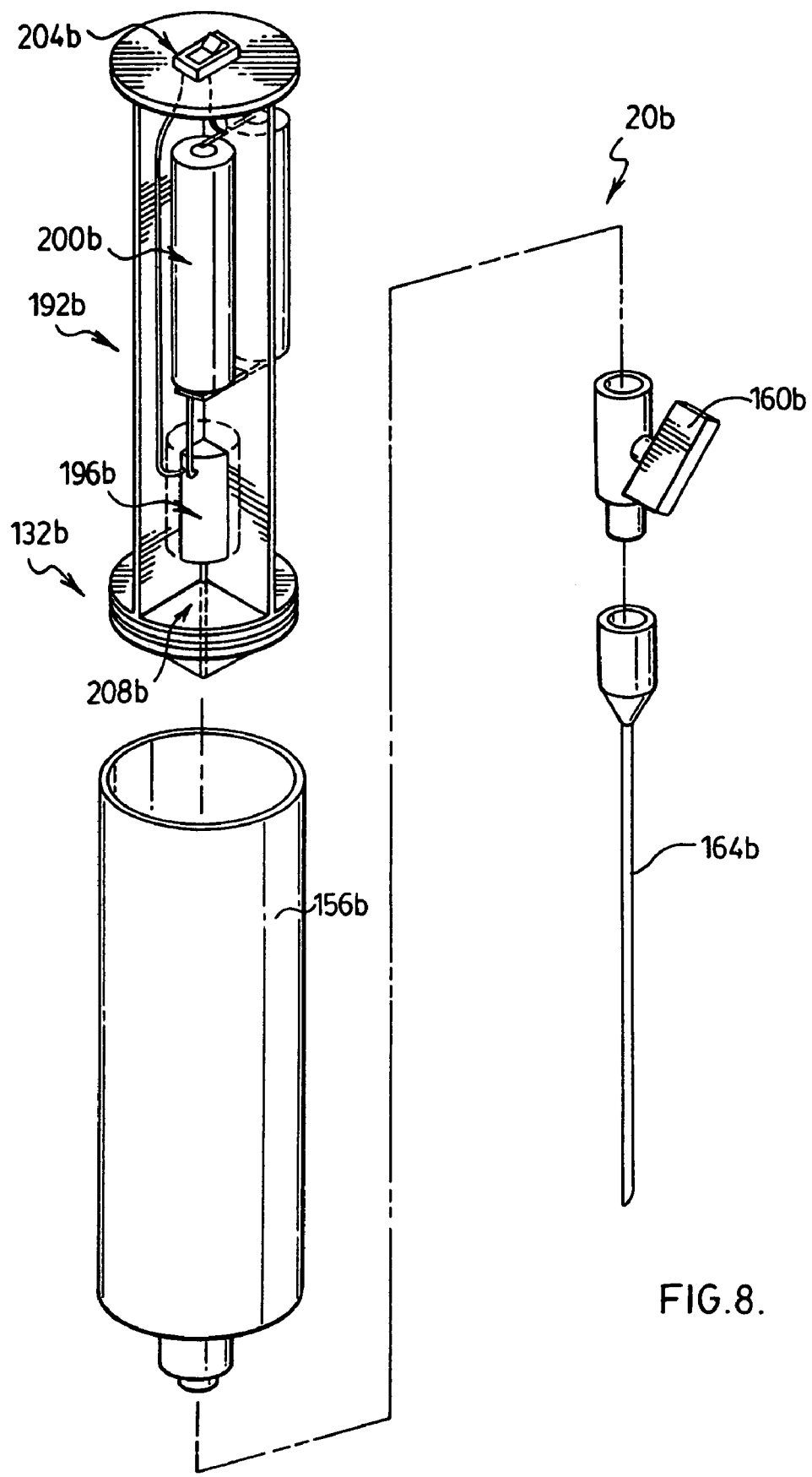
FIG. 8 shows an apparatus for administering a gas into a tissue in accordance with another embodiment of the invention.

Referring now to FIG. 8, an apparatus for administering a therapeutic agent into tissue is indicated generally at 20b. Apparatus 20b is a self-contained, portable version of apparatuses 20 and 20a. Specifically, apparatus 20b includes a needle 164b and a two-way valve 160b that are substantially the same as needle 164a and valve 160a as described above. Apparatus 20b also includes a syringe 132b comprising a barrel 156b (or other chamber) and a plunger 192b (or other means to express the contents of the chamber). Plunger 192b is configured as a normal plunger on a syringe, but also includes an miniature ozone generator 196b mounted on the shaft of plunger 192b. In turn, ozone generator 196b is connected to a power supply 200b and an on-off switch 204b that is disposed on the exterior tip of the shaft of plunger 192b. A small channel 208b joins generator 196b to the opposite tip of the shaft of plunger 192b, such that when plunger 192b is disposed in barrel 156b, generator 196b is in communication with the interior of barrel 156b. In this manner, switch 204b can be activated and thereby cause ozone to be generated and fill barrel 156b. Of particular note, in the present embodiment ozone can be generated in either gaseous or liquid form.

While switch 204b is activated, it is generally desired to have valve 160b placed in the closed position to prevent ozone from flowing from barrel 156b into needle 164b. Once a sufficient or otherwise desired amount of ozone has been generated and filled barrel 156b, switch 204b is turned "off" to discontinue generation of ozone, and then apparatus 20b is used in much the same manner as administrator 32 as described above in relation to FIGS. 2 and 3. The ozone generator 196b can be provided in a variety of sizes, capable of delivering a range of ozone volumes, for example from about one cc to about five cc, but could be made to generate volumes of ozone liquid or gas form of about 0.1 cc to about one liter.

Figure 9:
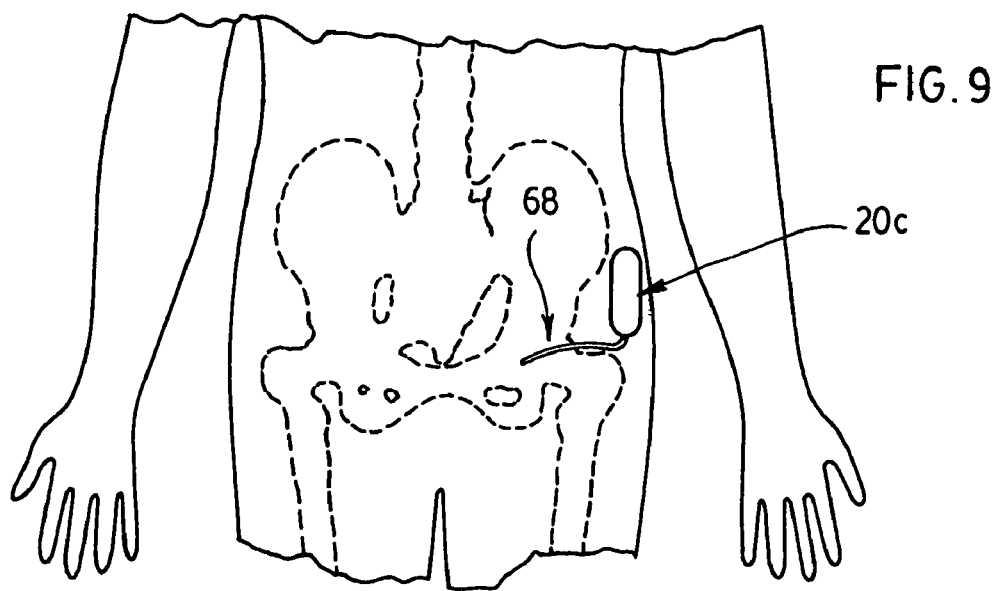
FIG. 9 shows an apparatus for administering a therapeutic agent into a hip region in accordance with another embodiment of the invention.
Figure 10:
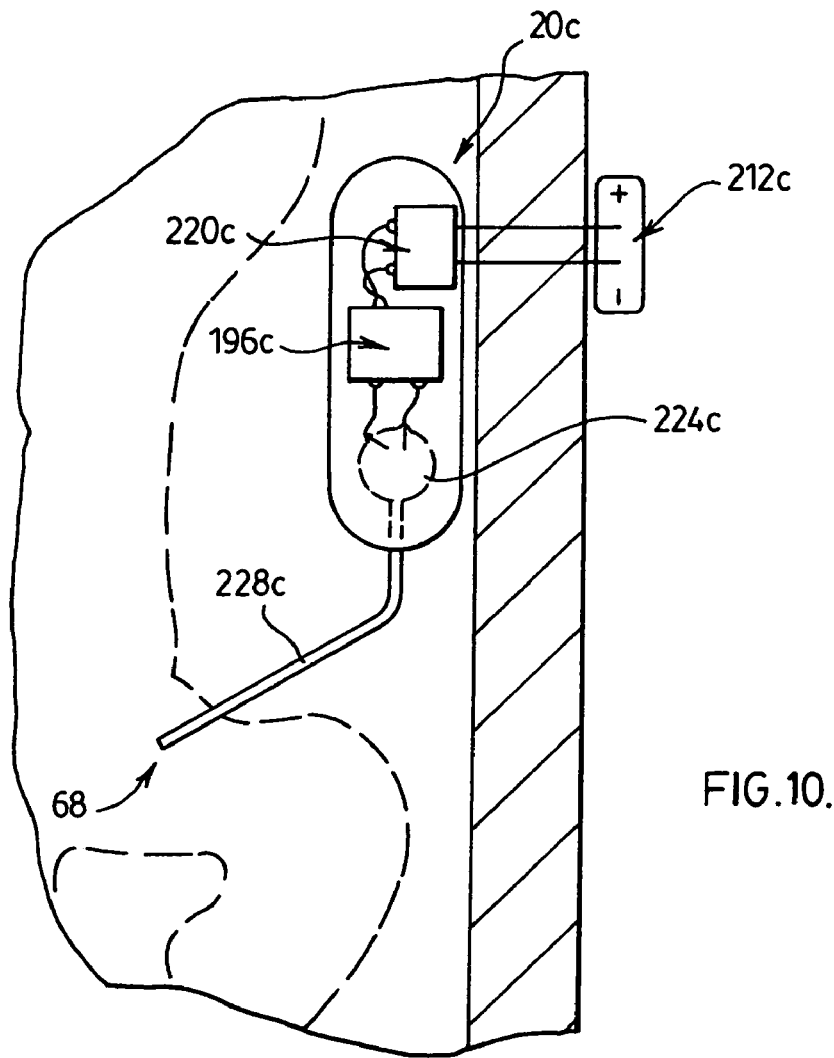
FIG. 10 shows the apparatus of FIG. 9 in greater detail.
Figure 11:
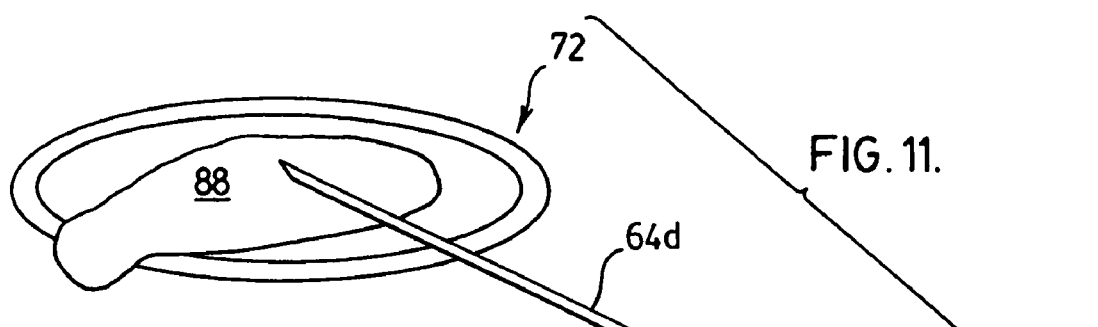
FIG. 11 shows an infusion wire through which a therapeutic agent can be administered.
Figure 12:
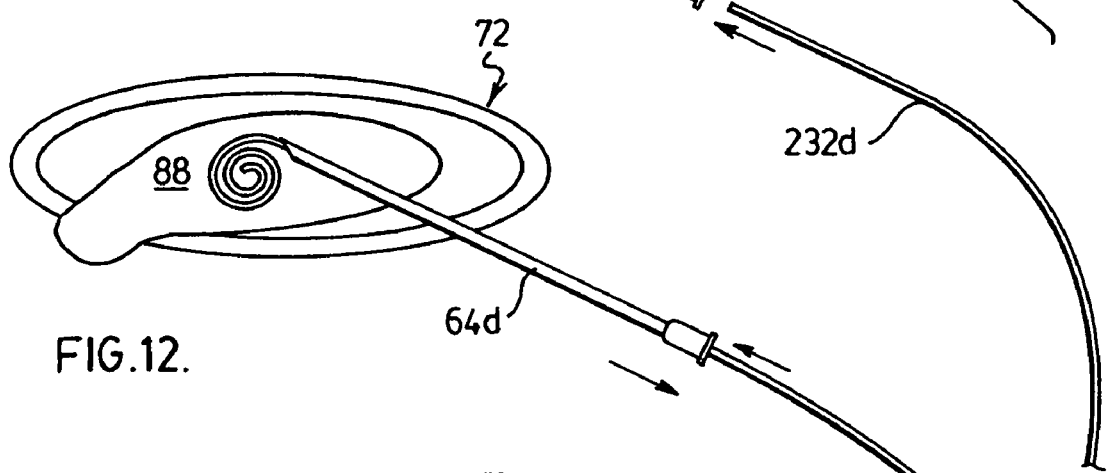
FIG. 12 shows the infusion wire being passed through a needle towards the centre of a herniated disc.
Figure 13:
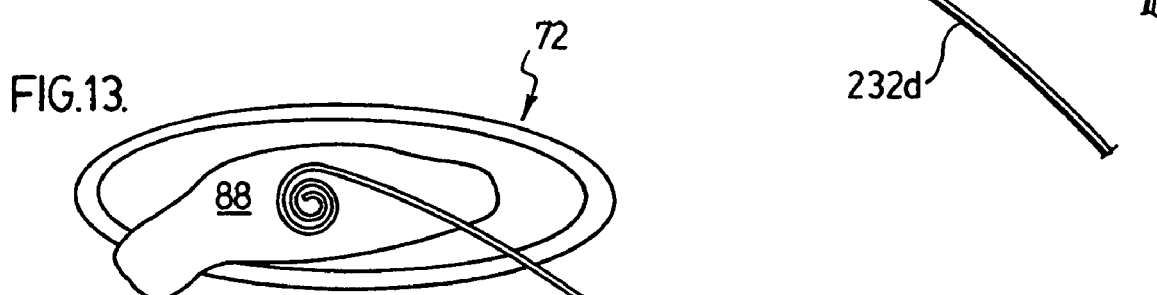
FIG. 13 shows the infusion wire being placed in centre of a herniated disc with the needle having been removed.

Referring now to FIGS. 9 and 10, an apparatus for administering a therapeutic agent into tissue is indicated generally at 20c. Apparatus 20c is a self-contained, implantable version of apparatuses 20, 20a and 20b. As shown in FIG. 9, apparatus 20c is implanted subcutaneously proximal to hip 68. In a present embodiment, apparatus 20c includes a separate, external switchable power supply 212c that is disposed just above the skin of the patient and is thereby activatable on demand by the patient. Power supply 212c connects to a miniature ozone generator 196c disposed percutaneously. In turn, generator 196c is connected to a oxygen source 220c, such that when power supply 212c is "on", generator 196c will interact with source 220c of either oxygen or sterile water, to generate ozone in either in liquid or gaseous form, inside a cavity 224c. In turn, cavity 224c is connected to a catheter 228c, which interconnects with cavity 224c with the tissue inside hip 68 to which the ozone is being administered to relieve pain associated therewith.

As a variation of apparatus 20c, power supply 212c can be disposed subcutaneously, and a wireless switching means can be disposed on the outside of the patient, such as a magnetic switch or other types of wireless means for activating or deactivating the ozone generator. Advantageous to this technique is that the overall use of needles is diminished, and thus beam hardening artifacts that are generated by metallic objects that can prevent proper visualization of the disc details (as might occur when doing injections by means of image guidance, and as may be done in certain other embodiments herein,) are reduced. In sum, by reducing the use of needles, visualization is improved and allows the dorsal root ganglion to be clearly seen.

Figure 14:
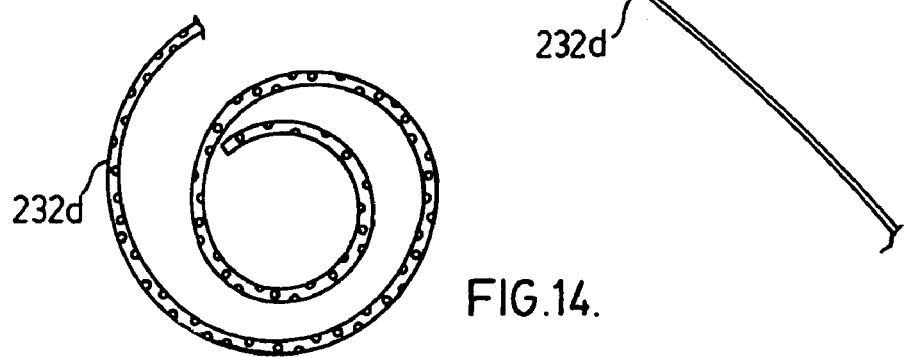
FIG. 14 shows the infusion wire of FIG. 11 in greater detail.

Referring now to FIGS. 11-14, in another variation an infusion wire 232d is passed through needle 168d until it coils inside nucleus pulposus 88 (or other tissue area for treatment.) Since infusion wire 232d is perforated along its length, as shown in FIG. 14, once a desired or sufficient amount of wire 232d has been inserted into nucleus pulposus 88, an ozone source can be connected to the opposite end of the infusion wire 232d and injected into nucleus pulposus 88 via the infusion wire. Due to the perforations along infusion wire 232d, ozone is dispersed more readily into nucleus pulposus 88.

Figure 15:
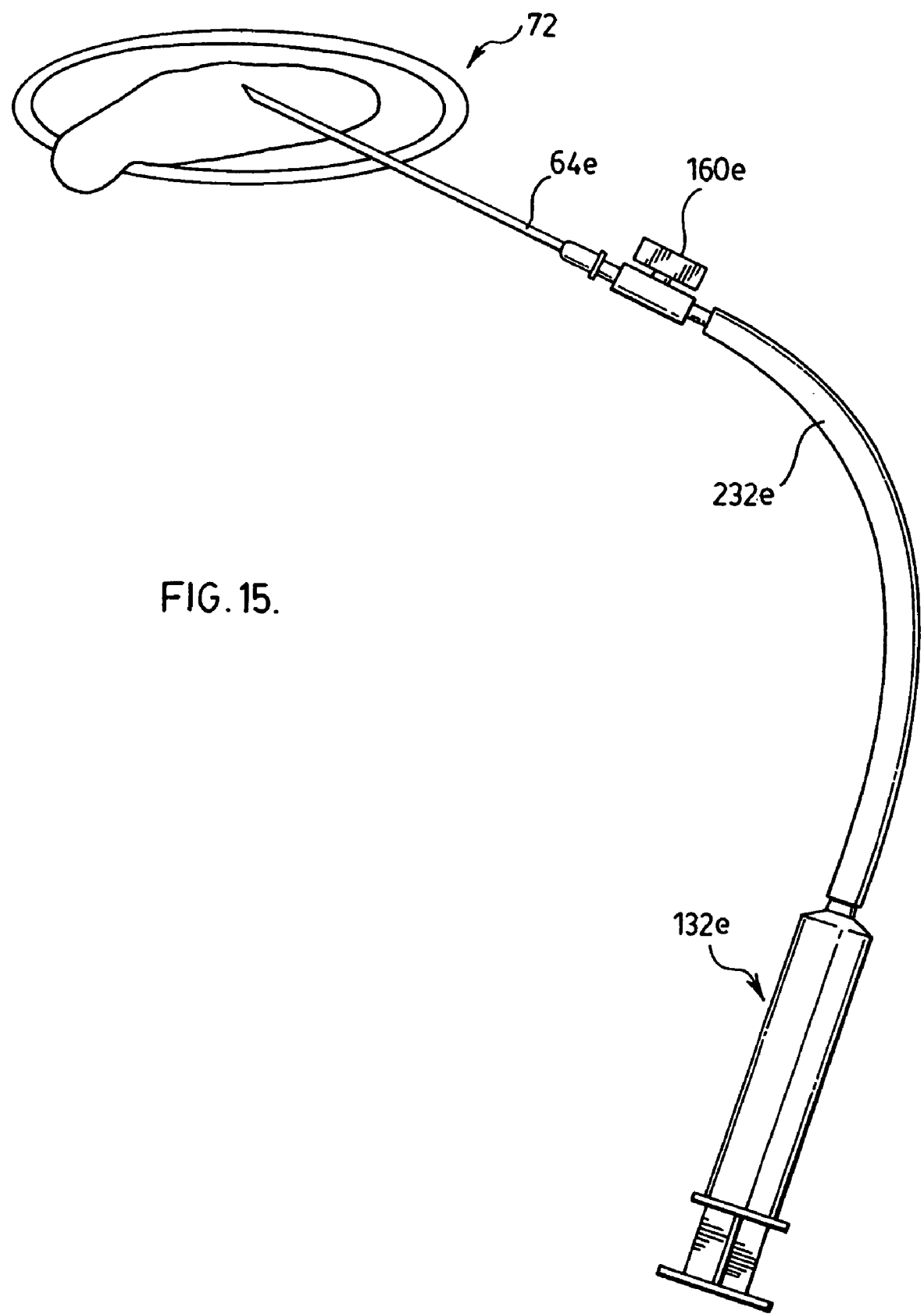
FIG. 15 shows an apparatus for administering a therapeutic agent into a tissue in accordance with another embodiment of the invention.

Referring now to FIG. 15, in another variation of the foregoing embodiments, it can be seen that various other configurations of how administration of the ozone are within the scope of the invention. Specifically, FIG. 15 shows a syringe 132e connected to a valve 160e via tubing 232e.

In another embodiment of the invention, a kit of parts for performing an injection of medical ozone for the treatment of a herniated disc or the like. The kit includes a sterile tray with a number of compartments to hold:
- a disinfectant, drape and skin preparation material,
- lidocaine and a 10 cc syringe with a 22-G long needle,
- nonionic x-ray dye-for discogram such as Omnipaque 300 M,
- outer 16 or 18 G needle to act as the co-axial introducing needle,
- 20 or 22 G needle with possible side holes for injecting the ozone into the disc,
- outer large needle of 16-18 G for steroid injection (can also be used to inject ozone into the paraspinous soft tissue),
- an infusion wire for even distribution of the ozone into the disc space
- a charcoal ozone scavenger (a bottle with charcoal and 100% $O_2$),
- steroids and local anaesthetics contained in a vial, ready for injection,
- a source of ozone such as a generator, examples include the AOS-1M Medical Ozonator or AOS-1MS Stainless Medical Ozonator, or a disposable injector in which then ozone can be generated filled with ozone,
- a disposable filtered attachment for the syringe a one way stop cock attached to the ozone generator,
- connecting, non-compliant tubing of 20-30 cm in length to reduce radiation to the operator hands during injection under image guidance.
- a three-way stop cock linking the tubing to the charcoal ozone scavenger bottle
- a one-way stop cock linking the tubing to the syringe via the said disposable filtered adapter,
- pharmaceutical gel such as Povidone, and
- adhesive bandages with a gauze pad in the center, such as Band-aid, or small dressing.

In another embodiment of the invention, there is a method consisting of first introducing the patient into the computer tomography ("CT") scanner and performing a diagnostic CT scan in order to identify the herniated disc such as disc 72. The CT gantry is subsequently draped and readied, the skin is prepared and local anaesthesia is applied to the skin and adjacent soft tissue. An 16-18 G needle is pinned down to the disc level and a 22 G needle is inserted into the disc. A discogram is performed to check symptoms by injection of x-ray dye. The ozone apparatus (in the form of any of the previously described apparatus or such other apparatus as may now occur to those of skill in the art is subsequently switched on and the ozone/oxygen chosen. The ratio of ozone/oxygen mixtures to choose from are about 0 µg/ml, about, 10 µg/ml, about 30 µg/ml, about 40 µg/ml, or about 50 µg/ml. A presently preferred range is between about 10 µg/ml and about 34 µg/ml, but more preferably about 27 µg/ml to about 28 µg/ml. In other embodiments other gases or therapeutic agents can be used, such as pure oxygen if found to be therapeutically effective or desirable.

As a next step, the syringe is fitted with a disposable filtered attachment which is itself attached to 20-30 cm of non-compliant tubing fitted with a 3-way to cock on one end and a one-way stop cock on the other, such as that shown in FIG. 15. Ozone gas is then aspirated into the 10-cc syringe (can also use a calibrated cardiac syringe) via the disposable filtered adapter and the connecting tubing such that the entire dead space is filled with a known concentration of ozone. The total volume of deadspace should be known so appropriate amounts of ozone are actually injected to the desired area. CT fluoro imaging or the like can be subsequently used to inject the ozone into the disc and paraspinous soft tissues. An infusion wire with a stiff stylet could be used, as previously described. Once the ozone injection is completed, a stop cock on the connecting tubing is closed. All of the leftover ozone is injected into the charcoal scavenger or a pure oxygen tube/bottle attached to the connecting tubing via a Luer lock. Steroids are then injected through the coaxial outer large needle. Finally, all needles are removed, the skin is appropriately dressed and a bandage is used to cover the perforated skin.

In another embodiment of the invention, there is provided the combined intradiscal and periganglionic injection of medical ozone and periganglionic injection of steroids which has an cumulative effect and enhances the overall outcome of treatment.

While only specific combinations of the various features and components of the present invention have been discussed herein, it will be apparent to those of skill in the art that desired subsets of the disclosed features and components and/or alternative combinations of these features and components can be utilized, as desired. For example, other types of pain can be treated using the teachings herein. For example, joints, tendons, ligaments are other areas that can be treated. Another example includes irrigating a wound site, such as a colostomy, with ozone to reduce pain at the wound site. As another example, an implantable device could put into the teeth (or other dental area) of a patient, similar to apparatus 20c to reduce pain in the dental region. As another example is to irrigate a subcutaneous pouch for holding a pacemaker or the like for sterilization and/or treatment of pain and/or decrease of inflammation and such other advantage corresponding to the therapeutic agent as will occur to those of skill in the art.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A syringe for self-contained generation and administration of a therapeutic agent comprising:
    a barrel for holding said agent;
    a plunger for insertion into a first end of said barrel and expressing said agent from a second end of said barrel;
    a power supply integrally mounted coaxially with said plunger;

a therapeutic agent generator integrally mounted coaxially with said plunger and in communication with said barrel through a channel in said plunger, said generator connected to said power supply and mounted coaxially with said plunger; and a switch connected to said power supply such that when said switch is activated said therapeutic agent generator generates said therapeutic agent and fills said barrel therewith.

2. The syringe of claim 1 wherein said agent is ozone.

3. The apparatus of claim 2 wherein said ozone is gas and said generator is a medical ozone generator.

4. The apparatus of claim 2 wherein said ozone is a ratio of ozone ($O_3$) to oxygen ($O_2$).

5. The apparatus of claim 4 wherein said ratio of ozone to oxygen is about 1 μg/ml.

6. The apparatus of claim 4 wherein said ratio of ozone to oxygen is about 10 μg/ml.

7. The apparatus of claim 4 wherein said ratio of ozone to oxygen is about 20 μg/ml.

8. The apparatus of claim 4 wherein said ratio of ozone to oxygen is about 30 μg/ml.

9. The apparatus of claim 4 wherein said ratio of ozone to oxygen is about 40 μg/ml.

10. The apparatus of claim 4 wherein said ratio of ozone to oxygen is about 50 μg/ml.

11. The apparatus of claim 4 wherein said ratio of ozone in micrograms to oxygen in milliliters is between about 1 μg/ml and about 90 μg/ml.

12. The apparatus of claim 4 wherein said ratio of ozone in micrograms to oxygen in milliliters is between about 10 μg/ml and about 80 μg/ml.

13. The apparatus of claim 4 wherein said ratio of ozone in micrograms to oxygen in milliliters is between about 20 μg/ml and about 70 μg/ml.

14. The apparatus of claim 4 wherein said ratio of ozone in micrograms to oxygen in milliliters is between about 10 μg/ml and about 34 μg/ml.

15. The apparatus of claim 4 wherein said ratio of ozone in micrograms to oxygen in milliliters is between about 27 μg/ml to about 28 μg/ml.

* * * * *